United States Patent [19]
Herzig

[11] Patent Number: 5,866,707
[45] Date of Patent: Feb. 2, 1999

[54] PROCESS FOR PREPARING ORGANOSILICON COMPOUNDS HAVING SI-BONDED HYDROGEN ATOMS

[75] Inventor: Christian Herzig, Waging am See, Germany

[73] Assignee: Wacker-Chemie GmbH, Germany

[21] Appl. No.: 69,652

[22] Filed: Apr. 29, 1998

[30] Foreign Application Priority Data

Apr. 30, 1997 [DE] Germany .................. 197 18 470.7

[51] Int. Cl.[6] ........................................ C07F 7/08
[52] U.S. Cl. ..................... 516/451; 556/469; 556/474
[58] Field of Search .................. 556/451, 469, 556/474

[56] References Cited

U.S. PATENT DOCUMENTS

| | | |
|---|---|---|
| 4,292,434 | 9/1981 | Lindner et al. . |
| 5,097,054 | 3/1992 | Yamamoto et al. . |
| 5,241,034 | 8/1993 | Herzig et al. . |
| 5,272,243 | 12/1993 | Nakashima et al. ............... 556/451 X |
| 5,446,158 | 8/1995 | Cobb et al. . |
| 5,446,185 | 8/1995 | Cobb et al. ............................... 556/451 |
| 5,493,040 | 2/1996 | Cobb et al. ............................... 556/451 |
| 5,527,935 | 6/1996 | Stepp et al. . |
| 5,691,435 | 11/1997 | Herzig et al. . |

FOREIGN PATENT DOCUMENTS

| | | |
|---|---|---|
| 0110370 | 4/1987 | European Pat. Off. . |
| 0431173 | 6/1991 | European Pat. Off. . |
| 0694573 | 1/1996 | European Pat. Off. . |
| 0786463 | 7/1997 | European Pat. Off. . |
| 4332425 | 3/1995 | Germany . |
| 19522144 | 1/1997 | Germany . |

OTHER PUBLICATIONS

Derwent Abstract #97–053209 [06] corresponding to DE 19522144.
Chemical Abstracts vol. 123, 56277w (1995).

*Primary Examiner*—Paul F. Shaver
*Attorney, Agent, or Firm*—Brooks & Kushman P.C.

[57] ABSTRACT

A process for preparing organosilicon compounds having Si-bonded hydrogen atoms comprises, in a first step, reacting silanes of the general formula $R^1R_aSiX_{3-a}$, where R. is a monovalent hydrocarbon radical free from aliphatic multiple bonds, $R^1$ is a monovalent terminal unsaturated hydrocarbon radical, X is a halogen atom or a radical of the formula $-OR^2$, and a is 0 or 1; with organosilicon compounds having at least two Si-bonded hydrogen atoms per molecule; in the presence of catalysts which promote the addition of Si-bonded hydrogen to an aliphatic multiple bond; and removing excess silanes by distillation, where the ratio employed of aliphatic double bond in the silane to Si-bonded hydrogen in the organosilicon compound is from 1.0 to 2.0; and in a second step, reacting the resultant compounds having hydrolyzable groups with silanes of the general formula $H_bR_{3-b}SiZ$ or siloxanes of the general formula $H_bR_{3-b}SiOSiR_{3-b}H_b$ where Z is a halogen atom or a radical of the formula $-OR^3$; b is 1 or 2; and water; in the presence of catalysts which promote hydrolysis, where the ratio employed of Si atoms in the latter silanes or siloxanes to hydrolyzable groups X in the compounds obtained from the first step is from 0.8 to 5.0, with the proviso that the resultant organosilicon compounds having Si-bonded hydrogen atoms have on average at least 4 Si-bonded hydrogen atoms per molecule.

8 Claims, No Drawings

PROCESS FOR PREPARING ORGANOSILICON COMPOUNDS HAVING SI-BONDED HYDROGEN ATOMS

TECHNICAL FIELD

The invention relates to a process for preparing organosilicon compounds having Si-bonded hydrogen atoms.

DESCRIPTION OF RELATED ART

The crosslinking agents used for aliphatically unsaturated organopolysiloxanes are almost exclusively organopolysiloxanes having hydridomethylsiloxane units, in the simplest case hydridomethylpolysiloxane end-capped with triorganosiloxy groups. To increase reactivity, it has proven successful to incorporate dimethylsiloxane units between the hydridomethylsiloxane units, by equilibration. However, these measures are only very limited improvements.

In EP-A 694 573, multifunctional siloxane copolymers having Si-bonded hydrogen atoms are prepared by reacting siloxanes having Si-bonded hydrogen atoms with multifunctional olefins or olefinic siloxanes in less than an equivalent amount. A large number of Si-bonded hydrogen atoms are consumed during this reaction, yielding products with a concentration of Si-bonded hydrogen atoms generally less than 0.4% by weight. Such products are undesirable for use as a crosslinking agent in addition-curing formulations.

U.S. Pat. No. 5,446,185 and U.S. Pat. No. 5,097,054 describe the preparation of siloxanes having Si-bonded hydrogen atoms by a hydrolytic process, but this process produces only products having at most three Si-bonded hydrogen atoms per molecule. Such products are unsuitable as crosslinking agents.

Chemical Abstracts Vol. 123, 56277w (1995) discloses a process for preparing carbosiloxanes which can have up to six Si-bonded hydrogen atoms per molecule. Intermediates having SiCl groups are obtained by adding hydridochlorosilanes to unsaturated silanes, and these are reacted with tetramethyldisiloxane in a hydrolytic process.

SUMMARY OF THE INVENTION

The object of the present invention is to provide a process for preparing organosilicon compounds having Si-bonded hydrogen atoms, in which multifunctional organosilicon compounds having SiH groups in terminal M-siloxane units are obtained. The SiH-functional compounds crosslink rapidly, in the presence of catalysts which promote the addition of Si-bonded hydrogen to an aliphatic multiple bond, with organosilicon compounds which have radicals having aliphatic carbon-carbon multiple bonds.

DESCRIPTION OF PREFERRED EMBODIMENT

The invention provides a process for preparing organosilicon compounds having Si-bonded hydrogen atoms by, in a first step, reacting silanes (1) of the general formula $$R^1R_aSiX_{3-a}$$

where R may be identical or different and is a monovalent hydrocarbon radical having from 1 to 8 carbon atoms per radical, halogenated if desired, and free from aliphatic multiple bonds, where $R^1$ is a monovalent terminally unsaturated hydrocarbon radical having from 2 to 14 carbon atoms per radical, and where each X may be identical or different, and is a halogen atom or a radical of the formula $—OR^2$, where $R^2$ is an alkyl radical having from 1 to 8 carbon atoms per radical, which may be substituted with an ethereal oxygen atom, and where a is 0 or 1;

with organosilicon compounds (2) having at least two Si-bonded hydrogen atoms per molecule;

in the presence of catalysts (3) which promote the addition of Si-bonded hydrogen to an aliphatic multiple bond;

and removing excess silanes (1) by distillation, where the ratio employed of aliphatic double bond in silane (1) to Si-bonded hydrogen in organosilicon compound (2) is from 1.0 to 2.0; and in a second step, reacting the resultant compounds having hydrolyzable groups with silanes (4) of the general formula $$H_bR_{3-b}SiZ$$

or siloxanes (5) of the general formula $$H_bR_{3-b}SiOSiR_{3-b}H_b$$

where R is as stated above;

Z is a halogen atom or a radical of the formula $-OR^3$, where $R^3$ is a monovalent hydrocarbon radical having from 1 to 8 carbon atoms per radical, which may be substituted with an ethereal oxygen atom;

b is 1 or 2;

and water, in the presence of catalysts (6) which promote hydrolysis, where the ratio employed of Si atoms in silanes (4) or in siloxanes (5) to hydrolyzable groups X in the compounds obtained from the first step is from 0.8 to 5.0;

and optionally, in a third step, equilibrating the resultant organosilicon compounds having Si-bonded hydrogen atoms with organopolysiloxanes (7) having Si-bonded hydrogen atoms and selected from the class consisting of linear organopolysiloxanes having terminal triorganosiloxy groups, linear organopolysiloxanes having terminal hydroxyl groups, branched organopolysiloxanes having, if desired, hydroxyl groups, cyclic organopolysiloxanes and copolymers made from diorganosiloxane units and monoorganosiloxane units;

with the proviso that the resultant organosilicon compounds having Si-bonded hydrogen atoms have on average at least 4 Si-bonded hydrogen atoms per molecule.

The subject invention organosilicon compounds having Si-bonded hydrogen atoms preferably have a viscosity of from 10 to 100 mm²·s⁻¹ at 25° C., particularly preferably from 20 to 70 mm²·s⁻¹ at 25° C.

The subject invention organosilicon compounds having Si-bonded hydrogen atoms advantageously contain, on average per molecule, from 6 to 50 Si-bonded hydrogen atoms, preferably from 8 to 50 Si-bonded hydrogen atoms, and particularly preferably from 10 to 40 Si-bonded hydrogen atoms.

The subject invention organosilicon compounds having Si-bonded hydrogen atoms have a hydrogen equivalent weight of advantageously from 60 to 200 g per mole of Si-bonded hydrogen, preferably from 90 to 150 g per mole of Si-bonded hydrogen.

The radical R in the organosilicon compounds having Si-bonded hydrogen atoms is free from aliphatic multiple bonds, so that there is no internal crosslinking, which leads to lack of solubility.

Examples of radicals R are alkyl radicals such as methyl, ethyl, n-propyl, isopropyl, 1-n-butyl, 2-n-butyl, isobutyl, tert-butyl, n-pentyl, isopentyl, neopentyl and tert-pentyl; hexyl radicals such as n-hexyl; heptyl radicals such as n-heptyl; octyl radicals, such as n-octyl, and isooctyl radicals such as 2,2,4-trimethylpentyl; cycloalkyl radicals, such as cyclopentyl, cyclohexyl, cycloheptyl and methylcyclohexyl; aryl radicals such as phenyl; alkaryl radicals such as o-, m- and p-tolyl, xylyl and ethylphenyl, and aralkyl radicals such as benzyl, and α- and β-phenylethyl. The methyl radical is preferred.

Examples of halogenated radicals R are haloalkyl radicals such as 3,3,3-trifluoro-n-propyl, 2,2,2,2',2',2'-hexafluoroisopropyl and heptafluoroisopropyl, and haloaryl radicals, such as o-, m- and p-chlorophenyl.

Examples of radicals $R^1$ are alkenyl radicals such as vinyl, allyl, 5-hexenyl, 7-octenyl, 2-(4-vinylphenyl)ethyl, 1-(4-vinylphenyl)ethyl, 1-(3-vinylphenyl)ethyl, 2-(3-isopropenylphenyl)-2-methylethyl and 2-(4-isopropenylphenyl)-2-methylethyl. The vinyl radical is preferred.

Examples of alkyl radicals $R^2$ are methyl, ethyl, n-propyl, isopropyl, 1-n-butyl, 2-n-butyl, isobutyl and tert-butyl. The methyl and ethyl radicals are preferred. Examples of alkyl radicals $R^2$ which are substituted with an ethereal oxygen atom are the methoxyethyl and ethoxyethyl radicals.

Examples of hydrocarbon radicals $R^3$ are alkyl radicals, such as methyl, ethyl, n-propyl, isopropyl, 1-n-butyl, 2-n-butyl, isobutyl and tert-butyl, the methyl and ethyl radicals being preferred, and the radical of the formula —C(=CH$_2$)CH$_3$. Examples of alkyl radicals $R^3$ which are substituted with an ethereal oxygen atom are the methoxyethyl and ethoxyethyl radicals.

A preferred example of the halogen atom X is the chlorine atom.

Examples of radicals Z are —Cl, —Br, —OCH$_3$, —OC$_2$H$_5$ and —OC(=CH$_2$)CH$_3$. In the formula, a is preferably 0, and b is preferably 1.

The organosilicon compounds having Si-bonded hydrogen atoms and obtained by the novel process preferably contain, as terminal units, M-siloxane units of the formula $$H_aR_{3-a}SiO_{1/2} \quad (I)$$

having SiH groups, where R and a are as stated above.

A particularly preferred example of the terminal SiH-group-containing M-siloxane unit in the multifunctional organosilicon compounds according to the invention is the hydridodimethylsiloxane unit.

Examples of silanes (1) are vinylmethyldichlorosilane, vinyltrichlorosilane, 5-hexenylethyldibromosilane, 5-hexenyltrichlorosilane and 7-octenyltrichlorosilane.

The organosilicon compounds (2) used may be selected from the class consisting of the organo(poly)siloxanes, carbosilanes, carbosiloxanes, polysilanes and polysilanosiloxanes. The organosilicon compounds (2) may therefore have structural units of the formula Si—O—Si, Si—$R^4$—Si, Si—$R^4$—Si—O—Si, Si—Si or Si—SiO—Si, SiO—Si, where $R^4$ is a bivalent hydrocarbon radical having from 2 to 12 carbon atoms per radical, which may be interrupted by one or more separate oxygen atoms. The organosilicon compounds (2) may be linear, branched or cyclic and preferably have from 2 to 20 Si-bonded hydrogen atoms per molecule.

The organosilicon compounds (2) contain units with Si-bonded hydrogen atoms. Examples of siloxane units with Si-bonded hydrogen atoms are those of the formula HR$_2$SiO$_{1/2}$, H$_2$RSiO$_{12}$, or HRSiO, where R is as stated above. Other examples of units having Si-bonded hydrogen atoms are those of the formula HR$_2$Si—$R^4$—, —$R^4$—HRSi—$R^4$—, —HRSi—, or HR$_2$Si—, where R and $R^4$ are as stated above.

Examples of radicals $R^4$ are 1,2-ethylene, 1,4-butylene, 1,6-hexylene, 1,1-ethylene and 4-oxa-1,7-heptylene.

Preferred examples of organosilicon compounds (2) are siloxanes of the general formula

where

R is as stated above, and n is an integer from 1 to 10, in particular from 1 to 7.

The organosilicon compounds (2) used are preferably distillable siloxanes having a molecular weight $M_n$ of not more than 600, since these siloxanes can be removed by distillation after the first step. The organosilicon compounds (2) preferably have from 1 to 2% by weight of Si-bonded hydrogen.

In the first step of the novel process, it is possible to use one type of silane (1) or various types of silane (1). Further, in the first step of the novel process, it is possible to use one type of organosilicon compound (2) or various types of organosilicon compound (2).

In the first step of the novel process, the ratio employed of aliphatic double bond in silane (1) to Si-bonded hydrogen in organosilicon compound (2) is advantageously from 1.0 to 1.5, preferably from 1.0 to 1.2.

The catalysts (3) which promote the addition of Si-bonded hydrogen to an aliphatic double bond in the novel process may be the same catalysts as those which could be used hitherto for promoting the addition of Si-bonded hydrogen to an aliphatic multiple bond. The catalysts (3) are preferably a metal from the platinum metals group or a compound or complex from the platinum metals group. Examples of such catalysts are metallic and finely divided platinum, which may be on supports such as silica, alumina or active carbon; compounds or complexes of platinum, such as platinum halides, e.g. PtCl$_4$, H$_2$PtCl$_6$· 6H$_2$O, Na$_2$PtCl$_4$· 4H$_2$O, platinum-olefin complexes, platinum-alcohol complexes, platinum-alcoholate complexes, platinum-ether complexes, platinum-aldehyde complexes, platinum-ketone complexes, including reaction products of H$_2$PtCl$_6$· 6H$_2$O and cyclohexanone, platinum-vinylsiloxane complexes, such as platinum-1,3-divinyl-1,1,3,3-tetramethyldisiloxane complexes, with or without any detectable content of inorganically-bonded halogen, bis(gamma-picoline) platinum dichloride, trimethylenedipyridineplatinum dichloride, dicyclopentadieneplatinum dichloride, dimethyl sulfoxide-ethyleneplatinum(II) dichloride, cyclooctadieneplatinum dichloride, norbornadieneplatinum dichloride, gamma-picolineplatinum dichloride, cyclopentadieneplatinum dichloride, and also reaction products of platinum tetrachloride with olefin and primary amine or secondary amine or primary and secondary amine, for example according to U.S. Pat. No. 4,292,434, such as the reaction product made from platinum tetrachloride dissolved in 1-octene with secbutylamine, or ammonium-platinum complexes according to EP-B 110 370.

In the first step, the catalyst (3) is preferably used in amounts of from 1 to 50 ppm by weight (parts by weight per million parts by weight), preferably in amounts of from 5 to 20 ppm by weight, calculated in each case as elemental platinum and based on the total weight of silane (1) and organosilicon compound (2).

The first step is preferably carried out at the surrounding atmospheric pressure, i.e. at about 1020 hPa (abs.), but may also be carried out at higher or lower pressures. The first step is, furthermore, preferably carried out at a temperature of from 40° to 140° C., preferably from 60° to 120° C.

The concomitant use of inert organic solvents is possible in the first step, but not preferred. Examples of inert organic solvents are toluene, xylene, octane isomers, butyl acetate, 1,2-dimethoxyethane, tetrahydrofuran and cyclohexane.

The inert organic solvents which may be used concomitantly, if desired, are removed by distillation after the first step.

A preferred embodiment of the first step is to meter organosilicon compound (2) into a mixture made from silane (1) and catalyst (3).

The reaction products obtained from (1) and (2) after the first step preferably contain at least 6, preferably from 6 to 30, hydrolyzable groups X.

Examples of silanes (4) which are used in the second step of the novel process are dimethylchlorosilane, methylchlorosilane, chlorosilane, methylbromosilane, dimethylmethoxysilane, methylmethoxysilane, dimethylethoxysilane, diethylchlorosilane, dimethylisopropenoxysilane and methyldiisopropenoxysilane.

Examples of siloxanes (5) which are used in the second step of the novel process are 1,1,3,3-tetra-methyldisiloxane, 1,3-dimethyldisiloxane, 1,1,1,-3,3-pentamethyldisiloxane and 1,1-dimethyldisiloxane.

In the second step of the novel process, it is possible to use one type of silane (4) or various types of silane (4), and also one type of siloxane (5) or various types of siloxane (5).

The catalysts (6) which promote hydrolysis and are used in the second step of the novel process may be the same as those which have hitherto also been capable of promoting the hydrolysis of organosilicon compounds having hydrolyzable groups. The catalysts (6) used may be acids or bases, the acids being preferred. Examples of acids are hydrochloric acid, hydrobromic acid, sulfuric acid and perchloric acid, hydrochloric acid being preferred. Particular preference is given to hydrochloric acid in a concentration of from 1 to 20%.

In the second step, water is used, preferably in amounts of from 20 to 200 g, based on a mole of Si-bonded hydrolyzable group X.

In the second step of the novel process, the ratio of Si atoms in silanes (4) or siloxanes (5) to hydrolyzable groups in the compounds obtained from the first step and having hydrolyzable groups is advantageously from 1.0 to 4.0, preferably from 1.5 to 3.5.

In the second step, preferred procedures are either to premix the compounds obtained from the first step with silanes (4) and to hydrolyze these together by metering this mixture into acid, or to premix siloxanes (5) with acid and to meter in the compounds obtained from the first step.

The second step is preferably carried out at the surrounding atmospheric pressure, i.e. at about 1020 hPa (abs.), but may also be carried out at higher or lower pressures. The second step is, furthermore, advantageously carried out at a temperature of from 0° to 40° C., preferably from 10° to 25° C.

The work-up of the second step preferably takes place by separating off the aqueous phase and washing with water and buffer solution.

Excess silane (4) and siloxane (5) are advantageously separated off after the second step, preferably by distillation.

In the second step concomitant use may be made of inert organic solvents. Examples of inert organic solvents are cyclohexane, toluene, xylenes and lower ketones, such as acetone and butanone.

The inert organic solvents which may, if desired, be used concomitantly are separated off after the second step, preferably removed by distillation.

The organosilicon compounds obtained after the second step and having Si-bonded hydrogen atoms may be equilibrated in a third step with organosiloxanes (7), if desired having Si-bonded hydrogen atoms. If the equilibration is carried out, the organosilicon compounds according to the invention having Si-bonded hydrogen atoms preferably have at most ten units of the formula $$H_c R_d SiO_{4-c-d/2},\qquad\text{(IV)}$$

preferably at most five units of the formula (IV).
where
R is as stated above,
c is 0 or 1, d is 1 or 2, and the sum of c and d is 1 or 2.

The organopolysiloxanes (7), if desired having Si-bonded hydrogen atoms, are preferably those selected from the class consisting of linear organopolysiloxanes of the formula $$R'_3SiO(SiR'_2O)_rSiR'_3$$

having terminal triorganosiloxy groups,
where
R' is the same as R or is a hydrogen atom,
r is 0 or an integer from 1 to 500, preferably from 10 to 200;
of linear organopolysiloxanes of the formula $$HO(SiR'_2O)_sH$$

having terminal hydroxyl groups,
where
R' is as stated above and
s is an integer from 1 to 1000, preferably from 10 to 500;
of branched organopolysiloxanes, which may have hydroxyl groups, containing units of the formula $$R'_3SiO_{1/2},\ R'_2SiO\ \text{and}\ R'SiO_{3/2}$$

where
R' is as stated above;
of cyclic organopolysiloxanes of the formula $$(R'_2SiO)_t,$$

where
R' is as stated above and
t is an integer from 3 to 12;
and of copolymers made from units of the formula $$R'_2SiO\ \text{and}\ R'SiO_{3/2},$$

where R' is as stated above.
Preferred organopolysiloxanes (7) are those of the formulae $$R'_3SiO(SiR'_2O)_rSiR'_3\ \text{and}\ HO(SiR'_2O)_sH.$$

The ratio of quantities of the organosilicon compounds having Si-bonded hydrogen atoms and organopolysiloxanes (7) used in the optional equilibration depends entirely on the desired proportion of Si-bonded hydrogen atoms in the organosilicon compounds produced in the equilibration, and on the desired average chain length.

When equilibration is carried out, acid catalysts which promote the equilibration are preferably used. Examples of acid catalysts are sulfuric acid, phosphoric acid, trifluoromethanesulfonic acid, phosphonitride chlorides, and acid catalysts which are solid under the reaction conditions, such as acid-activated bleaching earth, acid zeolites, sulfonated carbon and sulfonated styrene-divinylbenzene copolymer. Phosphonitride chlorides are preferred. Phosphonitride chlorides are preferably used in amounts of from 5 to 1000 ppm by weight (=parts per million), in particular from 50 to 200 ppm by weight, based in each case on the total weight of the organosilicon compounds used and organopolysiloxanes (7) used.

The equilibration may be carried out at from 100° to 150° C. and at the surrounding atmospheric pressure, i.e. at about 1020 hPa (abs.). However, it is also possible to use higher or lower pressures if desired. The equilibration is preferably carried out in from 5 to 20% by weight, based on the total weight of the particular organosilicon compounds used and organopolysiloxanes (7) used, of solvents immiscible with water, such as toluene. The catalyst may be deactivated before working-up the mixture obtained from equilibration.

The novel process may be carried out in batches, semi-continuously or fully continuously.

The organosilicon compounds having Si-bonded hydrogen atoms and obtained by the novel process are preferably used in crosslinkable formulations comprising (A) organosilicon compounds which have radicals having aliphatic carbon-carbon multiple bonds, (B) organosilicon compounds having Si-bonded hydrogen atoms and prepared by the novel process, (C) catalysts which promote the addition of Si-bonded hydrogen to an aliphatic multiple bond and, if desired, (D) agents which inhibit the addition of Si-bonded hydrogen to an aliphatic multiple bond at room temperature.

The crosslinkable formulations containing the organosilicon compounds (B) according to the invention having Si-bonded hydrogen atoms are preferably used for producing coatings which repel sticky substances, e.g. for producing release papers.

The organosilicon compounds (A) used, which have radicals having aliphatic carbon-carbon multiple bonds, are preferably linear or branched organopolysiloxanes made up of units of the general formula

$$R_e^5 R_f^6 SiO_{4-e-f/2} \quad (V)$$

where

R$^5$ is a monovalent hydrocarbon radical free from aliphatic carbon-carbon multiple bonds and having from 1 to 18 carbon atoms per radical and R$^6$ is a monovalent hydrocarbon radical having at least one terminal aliphatic carbon-carbon multiple bond and from 2 to 12 carbon atoms per radical, e is 0, 1, 2 or 3, f is 0, 1 or 2 and the sum of e and f is 0, 1, 2 or 3, with the proviso that there is on average at least one radical R$^6$ per molecule and there are preferably at least 2 radicals R$^6$ per molecule.

Examples of radicals R$^5$ correspond to the examples for radicals R.

Examples of radicals R$^6$ are alkenyl radicals, such as the vinyl, 5-hexenyl, 2,4-divinylcyclohexylethyl, 3,4-divinylcyclohexylethyl, 2-propenyl, 3-butenyl and 4-pentenyl; and alkynyl radicals, such as ethynyl and 2-propynyl.

Organosilicon compounds (A) and examples thereof are described, for example, in DE-A-195 41 51 and in U.S. Pat. No. 5,241,034.

Constituent (B) is preferably used in amounts, in gram atoms of Si-bonded hydrogen per mole of Si-bonded radical having an aliphatic carbon-carbon multiple bond in constituent (A) of from 0.8 to 5.0, preferably from 0.8 to 2.5, particularly preferably from 1.0 to 2.0.

The constituent (C) used is preferably the abovementioned catalysts (3).

Catalyst (C) is preferably used in amounts of from 5 to 500 ppm by weight (parts by weight per million part by weight), in particular from 10 to 200 ppm by weight, calculated in each case as elemental platinum metal and based on the total weight of the organosilicon compounds (A) and (B).

Examples of further constituents which may be used concomitantly in the formulations according to the invention are agents which inhibit the addition of Si-bonded hydrogen to an aliphatic multiple bond at room temperature, termed inhibitors (D); agents for adjusting the peel force; solvents; adhesion promoters; and pigments. Examples of inhibitors (D) are described in DE-A-195 22 144. The inhibitor (D) is preferably used in amounts of from 0.01 to 10% by weight, based on the total weight of the organosilicon compounds (A) and (B)

Although the sequence of mixing of constituents (A), (B), (C) and, if desired, (D) is not critical, it has proven successful in practice to add the catalyst constituent (C) lastly to the mixture of the other constituents.

The crosslinking of the formulations according to the invention takes place advantageously at from 50° to 150° C., preferably from 70° to 120° C. An advantage of the formulations according to the invention is that rapid crosslinking is achieved even at low temperatures. The energy sources used for the crosslinking by application of heat are preferably heating cabinets, e.g. circulating-air drying cabinets, heating ducts, heated rolls, hotplates or radiated heat in the infrared range.

As well as by heating, the formulations according to the invention may also be crosslinked by irradiating with ultraviolet light or with UV and IR light. The ultraviolet light used is usually that of wavelength 253.7 nm. There is a large number of lamps on the market with ultraviolet light emission wavelength of from 200 to 400 nm and with preferred ultraviolet light emission wavelength of 253.7 nm.

The formulations according to the invention may be applied to the surfaces which are to be made nonstick with respect to sticky substances in any desired one of many known methods suitable for producing coatings from liquid substances, for example by dipping, brushing, pouring, spraying, roller coating and printing, e.g. using an offset gravure coating device, or by knife- or doctor-coating, or using an air brush.

The surfaces to be made nonstick with respect to sticky substances, and which can be treated in the context of the invention, may be surfaces of any desired substances solid at room temperature and 1012 mbar (abs.). Examples of such surfaces are those of paper, wood, cork and plastics films, e.g. polyethylene films or polypropylene films, woven and nonwoven fabric made from natural or synthetic fibers or glass fibers, ceramic objects, glass, metals, polyethylenecoated paper and board, including asbestos board. The polyethylene mentioned above may be high-, medium- or low-pressure polyethylene, respectively. Paper may be low-quality paper grades, such as absorbent papers, including raw paper, i.e. Kraft paper with a weight of from 60 to 150 g/m² and not pretreated with chemicals and/or natural polymeric materials, unsized papers, papers with a low degree of beating, papers containing mechanical woodpulp, unsatinized or uncalendered papers, papers which, through use of a dry glazing cylinder during their production and without further elaborate measures, are glazed on one side and are therefore termed "(one-side-)machine-glazed" papers, uncoated papers or papers produced from paper wastes, i.e. recycled papers. However, the paper to be treated according to the invention may, of course, also be high-quality grades of paper, such as low-absorbency papers, sized papers, papers with a high degree of beating, wood-free papers, calendered or satinized papers, glassines, parchmentized papers or precoated papers. The board may also be of high or lesser quality.

The formulations according to the invention are suitable, for example, for producing release papers, protective or backing papers and supporting or interleaving papers, including supporting or interleaving papers which are used during the production of, for example, cast films or decorative films, or of foams, including those made from polyurethane. The formulations according to the invention are moreover, for example, suitable for producing release boards, protective or backing boards and supporting or interleaving boards, release films, protective or backing films and supporting or interleaving films, and release fabrics, protective or backing fabrics and supporting or interleaving fabrics, for application to the reverse sides of self-adhesive tapes or self-adhesives adhesive films, or the inscribed sides of self-adhesive labels. The formulations according to the invention are also suitable for packaging material, such as that made from paper, board cartons, metal films and vessels, e.g. board, plastics, wood or iron, which is or are intended for storing and/or transporting sticky products, such as adhesives, sticky foods, e.g. cake, honey, confectionery and meat, bitumen, asphalt, greased materials and crude rubber. Another example of the use of the formulations according to the invention is its application to carriers for transferring layers of pressure-sensitive adhesive by the "transfer method".

The formulations according to the invention are suitable for producing the self-adhesive materials connected with the release paper, either by the off-line process or by the in-line process.

EXAMPLE 1 a) 332 g of a distilled equilibrated product of the average formulation $(HMe_2SiO_{1/2})_2(HMeSiO)_{3.3}$ (Me=methyl radical) and having about 1.6% by weight of Si-bonded hydrogen is metered into 900 g of vinyltrichlorosilane, which contains about 10 mg of platinum in the form of a platinum-1,3-divinyl-1,1,3,3-tetramethyldisiloxane complex, known as the Karstedt catalyst, which corresponds to the catalyst prepared in accordance with U.S. Pat. No. 3,775,452 (published on Nov. 27, 1973, Bruce D. Karstedt, General Electric Company). During the addition, the temperature at the bottom is allowed to rise continuously to about 120° C., and the reaction is allowed to continue for a further hour. The excess of silane is then distilled out in vacuo. This gives 1176 g of a siloxane with trichlorosilyl end groups and a chlorine equivalent weight of about 75 g/mole of Si-bonded chlorine, or a chlorine content of 47.3%. The siloxane contains no Si-bonded hydrogen.

b) 150 g of 1,1,3,3-tetramethyldisiloxane are stirred intensively with 20 ml of water. 56.3 g of the chlorosiloxane whose preparation is described above under a), and about 100 ml of water, are metered in over a period of one hour, the mixture being held by cooling at a temperature of from 20° to 25° C. Stirring is continued at room temperature for two more hours, and the aqueous phase is separated off, and washing is carried out twice with on each occasion 200 ml of water and with phosphate buffer until neutral. The resultant hydridocarbosiloxane is freed from minor volatile constituents at 110° C. in vacuo. This gives 78 g of a clear oil having a viscosity of 47 mm²/s at 25° C. and having hydridodimethylsiloxy groups. The hydridocarbosiloxane contains 8.7 g of Si-bonded hydrogen per kg.

EXAMPLE 2

105 g of 1,1,3,3-tetramethyldisiloxane are stirred intensively with 20 ml of water. 56.3 g of the chlorosiloxane whose preparation is described in Example 1 under a), and 100 ml of water, are metered in simultaneously from separate vessels within about 30 minutes, the temperature being held by cooling at about 25° C. After stirring has continued for two hours, the phases are separated. The siloxane phase is washed twice with on each occasion 200 ml of water and then with phosphate buffer until neutral. Volatile constituents are removed at 110° C. in vacuo. This gives 70 g of a clear oil having a viscosity of 55 mm²/s at 25° C. The siloxane having hydridodimethylsiloxy groups contains 8.6 g of Si-bonded hydrogen per kg.

EXAMPLE 3 a) The method of operation described in Example 1 under a) is repeated, but with the alteration that, instead of the equilibrated H-siloxane product used there, use is made of 586 g of a siloxane of the average formulation $(Me_3SiO_{1/2})_2(HMeSiO)_{3.3}$ (Me=methyl radical) having 0.9% by weight of Si-bonded hydrogen. 1413 g of a siloxane having trichlorosilyl end groups, and in which Si-bonded hydrogen is no longer detectable, is obtained after carrying out and working up the reaction in a similar manner. The chlorosiloxane contains 39.0% by weight of Si-bonded chlorine and therefore has a chlorine equivalent weight of 91 g/mole of Si-bonded chlorine.

b) As described in Example 1 under b), 68 g of the chlorosiloxane whose preparation is described above under a) is reacted with the same amounts of disiloxane and water and worked up in the same way. This gives 90 g of a clear oil having a viscosity of 41 mm²/s at 25° C. and which has hydridodimethylsiloxy groups. The oil contains 7.6 g of Si-bonded hydrogen per kg.

Having now fully described the invention, it will be apparent to one of ordinary skill in the art that many changes and modifications can be made thereto without departing from the spirit or scope of the invention as set forth herein.

What is claimed is:

1. A process for preparing organosilicon compounds having Si-bonded hydrogen atoms, which comprises:

in a first step, reacting silanes (1) of the general formula $$R^1R_a SiX_{3-a}$$

where each R may be identical or different and is a monovalent, optionally halogenated hydrocarbon radical having from 1 to 8 carbon atoms per radical and free from aliphatic multiple bonds;

$R^1$ is a monovalent terminally unsaturated hydrocarbon radical having from 2 to 14 carbon atoms per radical; and each X may be identical or different and is a halogen atom or a radical of the formula —$OR^2$, where $R^2$ is an alkyl radical having from 1 to 8 carbon atoms per radical; which may be substituted with an ethereal oxygen atom; and a is 0 or 1;

with organosilicon compounds (2) having at least two Si-bonded hydrogen atoms per molecule; in the presence of catalysts (3) which promote the addition of Si-bonded hydrogen to an aliphatic multiple bond;

and removing excess silanes (1) by distillation;

where the ratio employed of aliphatic double bond in silane (1) to Si-bonded hydrogen in organosilicon compound (2) is from 1.0 to 2.0;

in a second step, reacting the compounds having hydrolyzable groups obtained in said first step with silanes (4) of the general formula $$H_bR_{3-b}SiZ$$

or siloxanes (5) of the general formula $$H_bR_{3-b}SiOSiR_{3-b}H_b$$

where R is as stated above;

Z is a halogen atom or a radical of the formula —$OR^3$, where $R^3$ is a monovalent hydrocarbon radical having from 1 to 8 carbon atoms per radical which may be substituted with an ethereal oxygen atom;

b is 1 or 2;

and water; in the presence of catalysts (6) which promote hydrolysis, where the ratio employed of Si atoms in silanes (4) or in siloxanes (5) to hydrolyzable groups X in the compounds obtained from the first step is from 0.8 to 5.0;

and optionally, in a third step, equilibrating the organosilicon compounds having Si-bonded hydrogen atoms obtained in said second step with organopolysiloxanes (7) having Si-bonded hydrogen atoms and selected from the group consisting of linear organopolysiloxanes having terminal triorganosiloxy groups; linear organopolysiloxanes having terminal hydroxyl groups; branched, optionally hydroxyl group-substituted organopolysiloxanes; cyclic organopolysiloxanes; and copolymers made from diorganosiloxane units and monoorganosiloxane units, with the proviso that the resultant organosilicon compounds having Si-bonded hydrogen atoms have on average at least 4 Si-bonded hydrogen atoms per molecule.

2. A process as claimed in claim 1, wherein vinyl trichlorosilane is used as silane (1).

3. A process as claimed in claim 1 wherein siloxanes of the general formula $$HR_2SiO(HRSiO)_nSiR_2H$$

are used as the organosilicon compound (2), where R is as stated in claim 1 and n is an integer from 1 to 10.

4. A process as claimed in claim 2 wherein siloxanes of the general formula $$HR_2SiO(HRSiO)_nSiR_2H$$

are used as the organosilicon compound (2), where R is as stated in claim 1 and n is an integer from 1 to 10.

5. A process as claimed in claim 1, wherein 1,1,3,3-tetramethyldisiloxane is used as siloxane (5).

6. A process as claimed in claim 2, wherein 1,1,3,3-tetramethyldisiloxane is used as siloxane (5).

7. A process as claimed in claim 3, wherein 1,1,3,3-tetramethyldisiloxane is used as siloxane (5).

8. A process as claimed in claim 4, wherein 1,1,3,3-tetramethyldisiloxane is used as siloxane (5).

* * * * *